(12) United States Patent
Weinberger et al.

(10) Patent No.: US 11,058,750 B2
(45) Date of Patent: Jul. 13, 2021

(54) COMPOSITIONS AND METHODS FOR TREATMENT OF OCULAR DISEASES

(71) Applicants: Dov Weinberger, Tel Aviv (IL); Tami Livnat, Savyon (IL); Yael Nisgav, Ramat Hasharon (IL)

(72) Inventors: Dov Weinberger, Tel Aviv (IL); Tami Livnat, Savyon (IL); Yael Nisgav, Ramat Hasharon (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 167 days.

(21) Appl. No.: 15/780,294

(22) PCT Filed: Jan. 12, 2016

(86) PCT No.: PCT/IB2016/057245
§ 371 (c)(1),
(2) Date: May 31, 2018

(87) PCT Pub. No.: WO2017/093923
PCT Pub. Date: Jun. 8, 2017

(65) Prior Publication Data
US 2018/0271958 A1 Sep. 27, 2018

Related U.S. Application Data

(60) Provisional application No. 62/262,394, filed on Dec. 3, 2015.

(51) Int. Cl.
*A61K 38/48* (2006.01)
*A61K 45/06* (2006.01)
*A61P 27/02* (2006.01)

(52) U.S. Cl.
CPC .......... *A61K 38/4866* (2013.01); *A61K 45/06* (2013.01); *A61P 27/02* (2018.01); *C12Y 304/21069* (2013.01)

(58) Field of Classification Search
None
See application file for complete search history.

(56) References Cited

U.S. PATENT DOCUMENTS

| 5,516,650 A | 5/1996 | Foster et al. |
| 5,921,998 A | 7/1999 | Tano et al. |

(Continued)

FOREIGN PATENT DOCUMENTS

| CA | 2531695 A1 | 1/2005 |
| EP | 1567199 B1 | 7/2014 |

(Continued)

OTHER PUBLICATIONS

Ambati et al., Neuron 75(1): 26-39 (2012).*

(Continued)

*Primary Examiner* — Erin M. Bowers
(74) *Attorney, Agent, or Firm* — Browdy and Neimark, PLLC

(57) ABSTRACT

Use of activated protein C (APC) for treatment and prevention of ocular diseases, disorders or conditions associated with retinal leakage and CNV such as age-related macular degeneration, optionally in combined therapy with anti-angiogenesis, anti-inflammatory, immunosuppressive, and anti PDGF agent.

7 Claims, 5 Drawing Sheets

(56) References Cited

U.S. PATENT DOCUMENTS

| | | | |
|---|---|---|---|
| 6,436,397 B1 | 8/2002 | Baker et al. | |
| 6,656,490 B1* | 12/2003 | Steinemann | A61K 38/4866 424/427 |
| 6,756,208 B2* | 6/2004 | Griffin | A61K 31/739 435/13 |
| 7,498,305 B2 | 3/2009 | Griffin et al. | |
| 9,192,657 B2 | 11/2015 | Griffin et al. | |

FOREIGN PATENT DOCUMENTS

| | | |
|---|---|---|
| EP | 1651252 B1 | 11/2014 |
| JP | 2009196927 | 9/2009 |
| WO | 03/075834 A2 | 9/2003 |
| WO | 2013025846 A2 | 2/2013 |
| WO | 2015052104 A1 | 4/2015 |

OTHER PUBLICATIONS

Yano et al., Clin. Cancer Res. 12(10): 3003-3009 (2006).*
Database WPI, Week 200959 Thomson Scientific, London, GB; AN 2009-N13588 & JP 2009 196927 A (ZH Kagaku&Kessei Ryoho Kenkyusho) Sep. 3, 2009 (Sep. 3, 2009).
Zhao-Jiang Du et al: "Activated Protein C Rescues the Retina from Ischemia-Induced Cell Death", Investigative Opthalmology & Visual Science, vol. 52, No. 2, Feb. 23, 2011 (Feb. 23, 2011), p. 987.
Kamei, Motohiro et al.: "Intravitreal Activated Protein C Injection as A Novel Treatment for Isohemic Central Retina Vein Occlusion", Investigative Ophthalmology & Visual Science, vol. 55.13 Apr. 15, 2014 (Apr. 15, 2014), pp. 3869-8869.
Deitch, Iris et al.: "The protective effect of activated protein C (APC) on cell permeability and laser ~induced CNV progression", Investigative Ophthalmology & Visual Science, vol. 57, No. 12 May 2, 2016 (May 2, 2016), pp. 2141-2141.
EP Application No. 16870093.8: Office Action dated Sep. 1, 2020.
EP Application No. 16870093.8: Extended European Search Report dated Apr. 30, 2019, 9 pages.
Hamish Ma Towler: "New technologies and drugs in the management of diabetic retinopathy", Practical Diabetes Jun. 12, 2014, vol. 31 No. 7, pp. 275-280a.
JP Application No. 2018-548296: Office Action dated Nov. 4, 2020 (Japanese) and English translation.
Joachim Wachtlin: "Classic Choroidal Neovascularization", Heimann/Kellner/Foerster, Atlas of Fundus Angiography, 2006 Georg Thieme Verlag KG, pp. 34-35.
John H. Griffin et al: "Activated protein C: biased for translation", Blood, 125(19), 2015, pp. 2898-2907.
Laurent Burnier and Laurent O. Mosnier: "Novel mechanisms for activated protein C cytoprotective activities Involving noncanonical activation of protease—activated receptor 3", Blood, 2013, vol. 122(5), pp. 807-816.
Mohammad Ali Sadiq: "Platelet derived growth factor inhibitors: A potential therapeutic approach for ocular neovascularization", Saudi Journal of Ophthalmology Jun. 29, 2015, pp. 287-291.
Nikita Minhas et al.: "Activated protein C utilizes the angiopoietin / Tie2 axis to promote endothelial barrier function", FASEB Journal Nov. 2016, vol. 24, No. 3, pp. 873-881.
Stefania Vetrano et al: "Unexpected role of anticoagulant protein C in controlling epithelial barrier integrity and intestinal inflammation", PNAS Dec. 6, 2011 vol. 108 No. 49, pp. 19830-19835.
Couch Steven M. and Bakri Sophie J: "Review of combination therapies for neovascular age-related macular degeneration". In: Seminars in ophthalmology. Taylor & Francis, 2011. pp. 114-120.
Kamei, Motohiro et al: "Reperfusion of large ischemic areas associated with central retinal vein occlusion: a potential novel treatment with activated protein C". JAMA ophthalmology, 2014, 132(3), pp. 361-362 [online].
Bradley John et al.: "Combination therapy for the treatment of ocular neovascularization". Angiogenesis, 2007, 10 (2), pp. 141-148 [online].
Livnat Tami et al.: "Activated protein C induces suppression and regression of choroidal Neovascularization—a murine model", Experimental Eye Research, 2010, 186 (1027605), pp. 1-8.
International Application No. PCT/IB2016/057245: International Search Report (ISR), dated Feb. 27, 2017.
International Application No. PCT/IB2016/057245: Written Opinion (WO), dated Feb. 27, 2017.
Database WPI, Week 200959 Thomson Scientific, London, GB; AN 2009-N13588 & JP 2009 196927 A (ZH Kagaku&Kessei Ryoho Kenkyusho) Sep. 3, 2009.
Zhao-Jiang Du et al: "Activated Protein C Rescues the Retina from Ischemia-Induced Cell Death", Investigative Opthalmology & Visual Science, 2011 (Feb. 23, 2011), 52(2), p. 987 [Retrieved from the Internet: <URL: http://iovs.arvojournals.org/article.aspx?articleid=2128323].
Kentaro Nishida et al: "Safety threshold of intravitreal activated protein-C", Graefe'S Archive for Clinical and Experimental Ophthalmology; Incorporating German Journal of Ophthalmology, Springer, Berlin, DE, vol. 249, No. 6, Nov. 24, 2010 (Nov. 24, 2010), pp. 833-888.
Kamei Motohiro et al.: "Intravitreal Activated Protein C Injection as A Novel Treatment for Ischemic Central Retinal Vein Occlusion", Investigative Ophthalmology & Visual Science, vol. 55(13) Apr. 15, 2014 (Apr. 15, 2014), pp. 3869-8869 [Retrieved from the Internet: <URL: http://iovs.arvojournals.org/article.aspx?articleid=2269331].
Deitch Iris et al: "The protective effect of activated protein C (APC) on cell permeability and laser ~induced CNV progression", Investigative Ophthalmology & Visual Science, vol. 57, No. 12, 2016 (May 2, 2016), pp. 2141-2141.
Journal of Japanese Ophthalmological Society, 2000, vol. 104 special issue, p. 209 (No. 285).

* cited by examiner

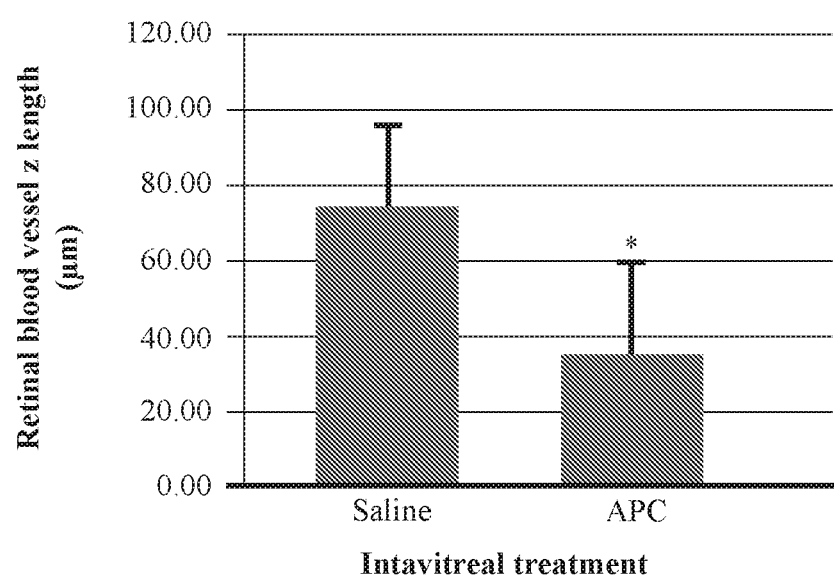

COMPOSITIONS AND METHODS FOR TREATMENT OF OCULAR DISEASES

TECHNICAL FIELD

The present invention, in some embodiments thereof, relates to treatment of ocular diseases, more particularly, but not exclusively, to the treatment or prevention of ocular disease associated with retinal leakage and choroidal neovascularization.

BACKGROUND

Choroidal neovascularization (CNV) is the creation of new blood vessels in the choroid layer of the eye, beneath the retina. Choroid is the area between the retina and the sclera (the white part of the eye) that supplies oxygen and nutrients to the eye. CNV occurs when new blood vessels start to grow in the choroid and break through Bruch's membrane, the barrier between the choroid and the retina (the substrate that supports the retina), into the retina and disrupt it. After choriocapillaries initially penetrate Bruch's membrane (BrM), invading vessels may regress or expand (CNV initiation). Next, during Early and Late CNV, the expanding vasculature usually spreads in one of three distinct patterns: in a layer between BrM and the retinal pigment epithelium (sub-RPE or Type 1 CNV), in a layer between the RPE (the black lining of the eye) and the photoreceptors (sub-retinal or Type 2 CNV) or in both loci simultaneously (combined pattern or Type 3 CNV) (see, Background art FIGS. 1A-1C). CNV leaking in the retina, e.g., bleeding and exudation accounts for some acute visual symptoms, most prominent of which is vision loss.

The location, the growth pattern and the type of CNV depend on the patient's age and the underlying disease with which it is associated. CNV is the leading cause of severe vision loss in various ocular diseases such as age-related macular degeneration (AMD), myopathy and angioid streaks.

Classic and occult CNV are distinguished, although they can appear in combined forms. Occult CNVs proliferate under the RPE. Classic CNVs are less frequent than the occult or mixed forms. It can occur in exudative age-related macular degeneration (AMD), but also secondary to other chorioretinal diseases. The diagnosis of a classic CNV requires an angiography, wherein it is defined as a clearly visible and well-demarcated hyperfluorescence in the early phase caused by vascular proliferations between the RPE and the neuroretina, with increasing leakage in the late phase of the angiography. The initial symptoms of classic CNV are metamorphopsia, deterioration in visual acuity, and central visual field defects. Ophthalmoscopic signs of CNV are grayish-white sub-retinal changes together with retinal edema, hard exudations, and subretinal and intraretinal hemorrhage. If the condition is not treated, progression with enlargement of the lesion and subsequent loss of photoreceptors will usually follow.

Most studies hypothesize that CNV primarily results from growth-factor effects or holes in BrM. However, a thorough computer simulation study (Shirinifard et al., 2012, *PLoS Computational Biology*, 8(5):1-32), based on three-dimensional simulations of multi-cell model of the normal and pathological maculae, recapitulate the three growth patterns of CNV (Types 1-3), under the hypothesis that CNV results from combinations of impairment of: (1) RPE-RPE epithelial junctional adhesion; (2) adhesion of the RPE basement membrane complex to BrM (RPE-BrM adhesion); and (3) adhesion of the RPE to the photoreceptor outer segments (RPE-POS adhesion). Key findings of the study were that when an endothelial tip cell penetrates BrM, one or more of the following may occur:

(1) RPE with normal epithelial junctions, basal attachment to BrM and apical attachment to POS would resists CNV.

(2) Small holes in BrM do not, by themselves, initiate CNV.

(3) RPE with normal epithelial junctions and normal apical RPE-POS adhesion, but weak adhesion to BrM (e.g. due to lipid accumulation in BrM) results in Early sub-RPE CNV. Reduced adhesion between pigmented retinal cells and Bruch's membrane is the type of CNV typical of aging.

(4) Normal adhesion of RBE to BrM, but reduced apical RPE-POS or epithelial RPE-RPE adhesion (e.g. due to inflammation) results in Early sub-retinal CNV. Reduced adhesion between neighboring pigmented retinal cells is typical of inflammation due to severe infection, and is a pattern of invasion seen in young adults.

(5) Simultaneous reduction in RPE-RPE epithelial binding and RPE-BrM adhesion results in either sub-RPE or sub-retinal CNV which often progresses to combined pattern CNV. These findings suggest that There are many causes to CNV most of which is synchronous or non-synchronous occurrence of an ocular disease or disorder, or a systemic disease or disorder such as inflammation or an autoimmune disease or disorder. However, since adhesion is an essential mechanism in maintaining the retina's structure, it seems that defects in adhesion dominate CNV initiation and progression, subsequently followed by retinal leakage.

The two main current treatments for CNV are either killing the invading blood vessels with drugs, mostly anti-angiogenesis agents, injected into the eye (most often also damaging the retina and killing needed blood vessels as well), or laser occlusion of the blood vessels, which can cause damaging retinal scars. Yet neither treatment still addresses the underlying problems that cause the blood vessels to invade, so relapses are common and many patients still lose vision within a year or two.

The protein C system provides negative-feedback regulation of host defense systems and can promote balanced regeneration of key tissue components. Key molecular players in the protein C system include protein C, protein S, thrombomodulin, endothelial protein C receptor (EPCR), PAR1, and PAR3. Protein C is a zymogen, or precursor, of the serine protease activated protein C (APC). Protein C is synthesized in the liver as a single-chain polypeptide that undergoes considerable processing to give rise to a two-chain molecule comprising heavy (Mr=40,000) and light (Mr=21,000) chains held together by a disulfide bond. The circulating two-chain intermediate is converted to the biologically active form of the molecule, APC, by the thrombin mediated cleavage of a 12-residue peptide (also know as the activation peptide) from the amino-terminus of the heavy chain. Inactivation of circulating APC by plasma serine protease inhibitors is a major mechanism for clearance of APC.

Pharmacologic APC promotes healing and tissue homeostasis in almost every organ of the body. APC initiates cell signaling that drives multiple, diverse, independent types of cellular activities, many of which are termed cytoprotective activities, comprising antiapoptotic and anti-inflammatory activities, favorable alterations of gene expression. APC promotes stabilization of endothelial and epithelial barriers to prevent vascular leakage (Griffin et al., Blood, 2015, 125(19):2898-2907; Vetrano et al., 2011, PNAS, 108(49): 1983019835).

The description above is presented as a general overview of related art in this field and should not be construed as an admission that any of the information it contains constitutes prior art against the present patent application.

SUMMARY

When the disruption of the homeostasis between the retinal pigment epithelium (RPE) and Bruch's membrane occurs, a vicious circle leads to the choroidal neo-angiogenesis also known as choroidal neovascularization (CNV). It is appreciated now that that cell adhesion is one of the keys to keeping blood vessels out of the retina and that a combination of defects in at least one types of adhesion, namely, RPE-RPE epithelial junctional adhesion; adhesion of the RPE basement membrane complex to Bruch's membrane; or adhesion of the RPE to the photoreceptor outer segments, is sufficient to determine the probability, pattern and rate of progression of CNV.

The present inventors have successfully addressed the yet unmet need to for therapies which restore normal adhesion in the eye thereby providing means to treat CNV and inhibit or prevent deleterious choroidal neo-vascular leakage in the retina. These therapies comprise the use of APC.

According to an aspect of some embodiments there is provided a method the treatment of an ocular disease, disorder or condition associated with retinal leakage and CNV comprising administering to a subject in need thereof an effective amount of APC.

According to an aspect of some embodiments there is provided a pharmaceutical composition comprising a pharmaceutically acceptable carrier and activated protein C (APC) for use in the therapy of an ocular disease, disorder or condition associated with retinal leakage and choroidal neovascularization (CNV).

According to an aspect of some embodiments there is provided the use of activated protein C (APC) for the manufacture of a medicament for the treatment of an ocular disease, disorder or condition associated with retinal leakage and choroidal neovascularization.

According to some embodiments, the therapy is treatment or prevention of an ocular disease, disorder or condition associated with retinal leakage and CNV.

According to some embodiments, the disease, disorder or condition associated with retinal leakage and CVN is a disease, disorder and condition caused directly by CVN, featuring development of CNV as a secondary stage or a complication thereof, or featuring CNV as a synchronous or asynchronous sequela thereof.

According to some embodiments, the ocular disease is selected from age-related macular degeneration (AMD), pathologic myopia, pseudoxanthoma elasticum with angioid streaks, noninfectious uveitis, infectious uveitis, inflammatory diseases of the optic nerve such as optic neurtis, papilledema, anterior and ischemic optic neuropath (AION), Behçet's disease and retinopathy; and said ocular disorder is selected from chronic inflammation, oxidative damage, drusen biogenesis, lipofuscin accumulation, abnormalities of Bruch's membrane, vascular changes in the eye that impede regulation of blood pressure and flow and create conditions of ischemia, physiologic aging, genetic factors and environmental factors; and said ocular condition is an accidental, occasional incidence in which CVN and retinal leakage develop following a traumatic injury of the retina and complications during an ophthalmic medical procedure.

According to some embodiments, the ocular disease is AMD.

According to some embodiments, APC comprises wild-type sequence of human APC, a functional partial sequence of APC, a derivative of APC or of a functional partial sequence thereof, or a variant of APC or of a functional partial sequence thereof.

According to some embodiments, the functional partial sequence comprises up to 95%, up to 90%, up to 85%, up to 80%, up to 75% of the wild-type APC amino acid sequence, and it maintains wild type or near wild type APC functionality.

According to some embodiments, the amino acid sequence of said APC variant is at least 70%, at least 80%, at least 85%, at least 90%, at least 95%, at least 98%, or 100% identical to the amino acid sequence of wild type APC.

According to some embodiments, APC and a pharmaceutical composition comprising it are use in combined therapy with one or more active agents selected from anti-angiogenesis, anti-inflammatory, anti-bacterial, immunosuppressive, anti PDGF, anti-fungal and anti-viral agent.

According to some embodiments, the anti-angiogenesis agent is anti-VEGF agent or platelet derived growth factor (PDGF) inhibitor, and said immunosuppressive agent is a steroid.

This Summary introduces a selection of concepts in a simplified form that are further described below in the Brief Description of the Drawings and the Detailed Description. This Summary is not intended to identify key features or essential features of the claimed subject matter, nor is it intended to be used to limit the scope of the claimed subject matter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments are herein described, by way of example only, with reference to the accompanying drawings. With specific reference now to the drawings in detail, it is stressed that the particulars shown are by way of example and for purposes of illustrative discussion of embodiments. In this regard, the description taken with the drawings makes apparent to those skilled in the art how embodiments may be practiced.

In the drawings:

FIGS. 6A-6C are (1 µm) distance Z stack images (6A-6B), and a graph (6C) of an exemplary flattened entire retina following laser photocoagulation and intravitreal injections of saline, or APC (1 µg/animal). Blood vessels are shown bright in the images.

DETAILED DESCRIPTION

Aspects of disclosed embodiments relate to the use of activated protein C (APC) in the therapy of ocular diseases more particularly, but not exclusively, to treatment of ocular diseases associated with choroidal neovascularization and retinal leakage.

Before explaining at least one embodiment in detail, it is to be understood that the disclosed embodiments are not necessarily limited in its application to the details set forth in the following description or exemplified by the Examples. The invention is capable of other embodiments or of being practiced or carried out in various ways.

Optimal retinal function requires an appropriate, tightly regulated environment. This regulation is ascertained by cellular barriers, created by tight junction proteins, which separate functional compartments, maintain their homeostasis, and control transport between them. Blood retinal barriers (BRB), particularly the outer barrier composed of retinal pigment epithelium (RPE), and the inner barrier between retinal microvascular endothelium, are highly dynamic structures, capable of rapidly responding to physiological requirements as well as to changing extrinsic conditions.

Figure 1A:
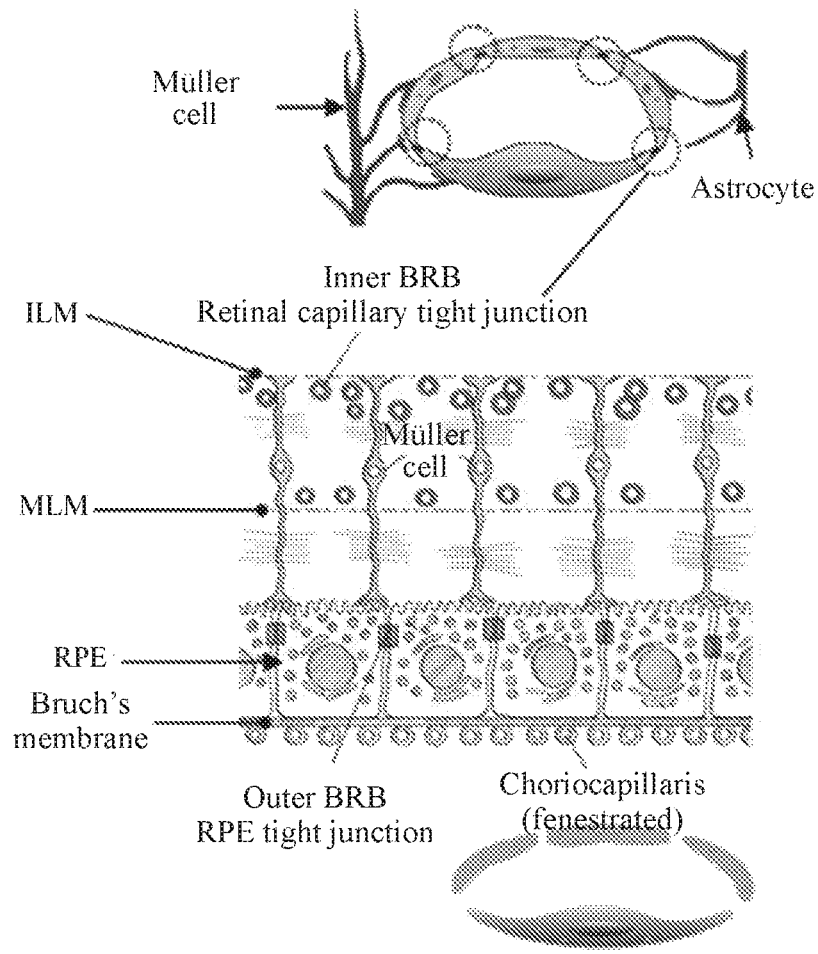
FIGS. 1A-1C are Background art schemes of the blood retinal barriers (BRBs) (1A), a normal structure of the retina (1B), and retina featuring choroidal neovascularization in age related macular degeneration (AMD) (1C)
Figure 1B:
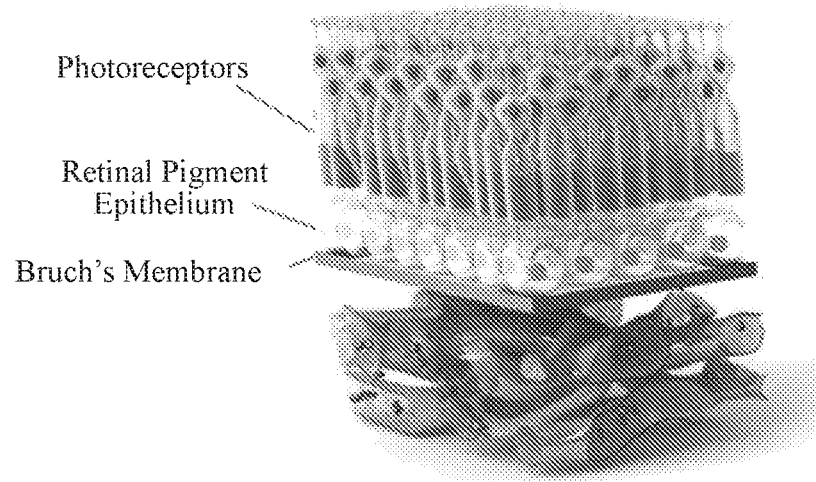
Figure 1C:
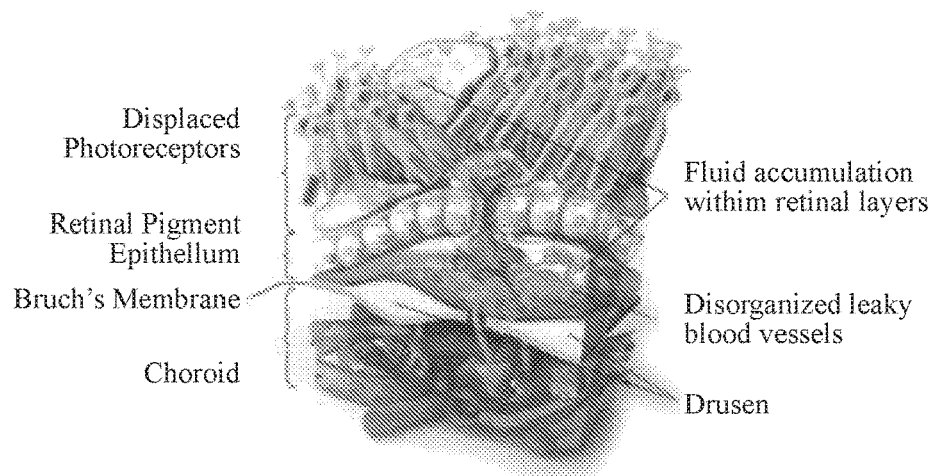
Figure 2A:
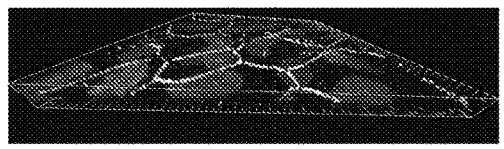
FIGS. 2A-2D are confocal microscope images of retinal pigment epithelium cells (ARPE-19) stained with rabbit anti ZO-1 antibody (bright) and NucBlue® (nuclear staining; light, round circular areas), following treatment with 0.0 µg/ml APC (control, 1A); 0.1 µg/ml APC (1B); 1 µg/ml APC (1C); or 10 µg/ml APC (1D)
Figure 2B:
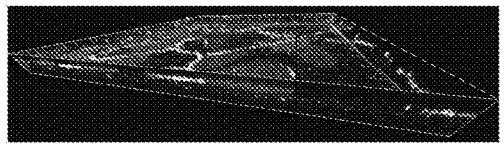
Figure 2C:
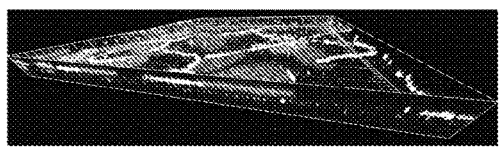
Figure 2D:
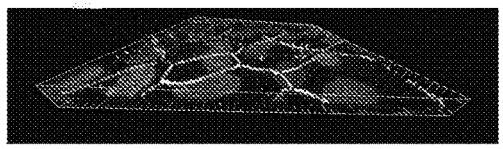

Most of the retinal diseases involve vascular leakage and breakage of the inner or outer BRBs. There are two types of neovascularization that occur in the retina and cause vision loss: retinal neovascularization (RNV) in which new vessels sprout from the retinal capillaries and invade the vitreous and neural retinal layers, and choroidal neovascularization (CNV), in which new vessels sprout from the choroidal vasculature and invade the sub-retinal space. CNV is a blinding complication of age-related macular degeneration (AMD) that manifests as the growth of immature choroidal blood vessels through Bruch's membrane followed by a damage to the BRB, where they can leak fluid or hemorrhage under the retina (see, Backround Art FIGS. 1B and 1C). CNV is the leading cause of severe vision loss in various ocular diseases other than AMD, for example, angioid streaks and high myopia.

The two main current treatments for CNV are either killing the invading blood vessels with anti-vascular endothelial growth factor (VEGF) agents (e.g Bevacizumab, Ranibizumab, Aflibercept), injected into the eye (most often also damaging the retina and killing needed blood vessels as well), or laser coagulation of the blood vessels, which can cause damaging retinal scars. Yet neither treatment still addresses the underlying problems that cause the blood vessels to invade. In addition, reduced therapeutic response to anti-VEGF agents most often follows repeated administration over time. Thus, relapses are common and many patients still lose vision within a year or two. Treatment directed against the cause of the disease yet remains difficult to accomplish, as the underlying etiology is very complex and elusive.

Activated protein C (APC) is a plasma serine protease with, inter alia, endothelial and epithelial barrier protective properties.

In search for treatment modalities that would meet the yet continuing need for treatment of CNV and prevention of retinal leakage, the present inventors have envisaged a barrier protective effect of APC on impaired adhesions in critical junctions of RPE in the retina, thus leading to retinal leakage and CNV prevention or amelioration.

The present inventors have devised in vitro and in vivo models to assess the protective effect of APC on RPE and BRBs, and successfully practiced a novel method of treating CNV based on intravitreal administration of APC.

As demonstrated in the Examples section that follows, in an in vitro model of human retinal pigment epithelial cells (ARPE-19), APC induced translocation of tight junction protein Zonula Occludens 1 (ZO-1) to the ARPE19 cell membrane and reduced RPE permeability of labeled dextran as compared to untreated cells (see, Examples 1 and 2 herein). In an in vivo model devised by the present inventors, CNV was induced by indirect diode laser photocoagulation on male C57BL/6J mice. Intravitreal injection of APC (1 µg/animal) immediately following injury dramatically reduced CNV area (Example 3, herein) as well as CNV volume and depth, as shown by 3-dimensional analysis (see, Example 4 herein). The APC effect was comparable to the effect of bevacizumab, the current treatment of choice for CNV.

The present inventors have further quantitated blood vessels formation following laser injury in mice, and have successfully demonstrated that APC reduced significantly the development and penetration of blood vassals from the choroid into the retina (see, Example 5 herein).

In an aspect of some embodiments, there is provided a method for preventing or treating ocular diseases, disorders and conditions associated with retinal leakage and choroidal neovascularization, the method comprising administering to a patient in need thereof an effective amount of activated protein C (APC).

"Activated protein C" as used herein is to be interpreted in a broad manner so as to encompass various forms of APC known in the art and those yet to be discovered. Non-limiting examples include: wild-type sequence of human APC; a polymorphic variant of human APC; an interspecies homolog of human APC; a functional partial sequence of wild-type human APC or of its polymorphic variant or interspecies homolog; a derivative of wild-type human APC or of its polymorphic variant, interspecies homolog or functional partial sequence; and a variant (mutant) of wild type human APC or of its polymorphic variant, interspecies homolog, or functional partial sequence. The term "administration of APC" as used herein refers to administration of one or more of these forms of APC, either combined in a single dosage form or administered consecutively in one or more separate dosage forms, each comprising one or more forms of APC as described herein.

The term "associated with choroid neovascularization" as used herein refers to a disease, disorder or condition caused directly by CVN, or disease, disorder or condition featuring development of CNV, for example, as a secondary stage or a complication thereof and, optionally, worsen, exacerbate or progress because of the CNV process. Diseases disorders or conditions featuring CNV as a synchronous or asynchronous sequela thereof, namely CNV resulting from earlier occurrence of such diseases or disorders, for example infectious or noninfectious diseases, are also diseases disorder or condition associated with CNV as defined herein.

Ocular diseases associated with CNV, treatable by the method described herein include, but are not limited to, age-related macular degeneration (AMD), pathologic myopia, and pseudoxanthoma elasticum with angioid streaks.

CNV and blood leakage in the retina can result from a myriad of inflammatory and non-inflammatory diseases of the choroid and the retina, such as, but not limited to, optic neurtis, and other inflammatory diseases of the optic nerve such as papilledema, anterior and ischemic optic neuropath (AION), blood vessels occlusion, Behçet's disease and diabetes complications such as retinopathy.

CNV can be the sequela of both infectious and noninfectious uveitis. In the infectious diseases, Toxoplasmosis (caused by the parasite *Toxoplasma gondii* and accounts for toxoplasmic retinochoroiditis), *Toxocara canis*, Tuberculosis, and viral retinopathies, can have CNV as synchronous or asynchronous sequela. Noninfectious uveitis associated with CNV includes, but not limited to, punctate inner choroidopathy (PIC), multifocal choroiditis (MFC), acute posterior multifocal placoid pigment epitheliopathy (APMPPE), serpiginous choroiditis (SC), presumed ocular histoplasmosis syndrome (POHS) and Vogt-Koyanagi-Harada (VKH) disease.

For example, CNV is commonly associated with MFC, which is found in 32 to 46% of patients, and in POSH, the primary cause of visual impairment is the occurrence of CNV in the macula, which results in exudation and subsequent scarring.

Bacteria can also affect the eye, and CNV can (although rarely) be one of the most severe sequela. The retinal colonization can occur by metastasizing the choroid during endocarditis, aortic valve infection, renal and bone abscess and intravenous drug abuse. The choroidal neovascular membrane typically grows near an active or quiescent choroidal granuloma. Classic CNV is generally the typical occurrence in bacterial endocarditis, which grows close to the primary chorioretinal lesion, or in neighboring area of an old atrophic scar.

Viruses have also been associated with CNV, predominantly as a late complication (Neri et al., 2009, *Middle East Afr J Ophthalmol.*, 16(4): 245-251), for example, the West Nile virus can cause an extensive ischemic capillaropathy in the macula that may develope into a choroidal neovascularization near a chorioretinal scar.

CNV can be a late sequela of Fungi, such as *Candida albicans, Cryptococcus neoformans* and *Aspergillus fumigatus*, that have been described as potential pathogen for the eye.

Ocular disorders associated with CNV which can benefit from treatment with APC in accordance with the embodiments of the method described herein include, but are not limited to, oxidative damage, drusen biogenesis, lipofuscin accumulation, abnormalities of Bruch's membrane, vascular changes in the eye that impede regulation of blood pressure and flow thus, limiting the exchange of nutrients and removal of metabolic waste and creating conditions of ischemia, physiologic aging, genetic factors (mutations in the complement pathway) and environmental factors (for example, smoking, irradiation, lack of vitamins and the like). For example, CNV may be secondary originating from an old chorioretinal scar.

"Conditions associated with CNV" as defined herein refer to accidental, occasional, one-time incidences in which CNV develops as a result of, for example, traumatic injury of the retina, complications during an ophthalmic medical procedure such as surgery, laser treatment or routine checkup, and the like.

The terms "therapy", "treatment", "treating", "treat" as used herein are interchangeable and refer to: (a) preventing a disease, disorder, or condition from occurring in a human which may be predisposed to the disease, disorder and/or condition but has not yet been diagnosed as having it; (b) inhibiting the disease, disorder, or condition, i.e., arresting its development; (c) relieving, alleviating or ameliorating the disease, disorder, or condition, i.e., causing regression of the disease disorder and/or condition; and (d) curing the disease, disorder, or condition. In other words, the terms "therapy", "treat," "treatment," and "treating," extend to prophylaxis, namely, "prevent," "prevention," and "preventing," as well as treatment per se of established conditions. Accordingly, use of the terms "prevent," "prevention," and "preventing," would be an administration of the active agent to a person who has in the past suffered from the aforementioned conditions, such as, for example, retinal leakage or CNV, but is not suffering from the conditions at the moment of the composition's administration.

Thus, the terms "treatment", "therapy" and the like include, but are not limited to, changes in the recipient's status. The changes can be either subjective or objective and can relate to features such as symptoms or signs of the disease, disorder or condition being treated. For example, if the patient notes improvement in visual acuity, reduced central visual field defects or decreased pain, then successful treatment has occurred. Similarly, if the clinician notes objective changes, such as by fluorescein angiography (FA), indocyanine green angiography (ICGA) or optical coherence tomography (OCT), then treatment has also been successful. Alternatively, the clinician may note a decrease in the size of lesions or other abnormalities upon examination of the patient (for example, grayish-white subretinal changes together with retinal edema, hard exudations, and subretinal and intraretinal hemorrhage). This would also represent an improvement or a successful treatment. Preventing the deterioration of a recipient's status is also included by the term. Therapeutic benefit includes any of a number of subjective or objective factors indicating a response of the condition being treated as discussed herein In some embodiments, the method of treating or preventing ocular diseases, disorder or conditions may include administrating to a subject in need thereof an effective amount of APC of from about 10 µg/ml to about 250 µg/ml, from about 10 µg/ml to about 150 µg/ml, from about 10 µg/ml to about 100 µg/ml, from about 20 µg/ml to about 100 µg/ml, from about 30 µg/ml to about 90 µg/ml, from about 30 µg/ml to about 80 µg/ml, from about 40 µg/ml to about 70 µg/ml, for example, about 60 µg/ml, per dose, including any subranges and any intermediate values therebetween.

In some of any of the embodiments, application of APC in the treatment of ocular diseases, conditions or disorders associated with CNV is affected by intravitreal administration, for example intravitreal injection.

Optionally, in accordance with these embodiments, while taking into consideration that fluids in the retina (vitreous) dilute APC administered in any of the effective amounts described herein by a factor of 20-50, a portion of about 0.02 ml to about 0.1 ml, about 0.03 ml to about 0.07 ml, about 0.04 ml to about 0.06 ml, preferably about 0.05 ml, including any subranges and any intermediate values therebetween, of APC diluted in an intraocular irrigating solution to any of the effective concentration ranges described above is prepared. Optionally, each portion is prepared, e.g., in insulin syringes and, optionally, stored e.g., at −70° C. until just before use. Optionally, eye drops, for example of 0.3% levofloxacine, are applied immediately after injection.

In some embodiments of the method, an effective amount of APC as described herein is topically applied to the eye.

The method of treating CNV and vascular leakage in the retina as described herein may benefit, for example provide a synergistic effect, when combined with other treatment modalities, particularly treatment modalities that address the prime motive or the trigger for development of CNV.

Taking into consideration that chronic subclinical inflammation and clinical inflammation of the retina and the choroid can be the basis for the pathogenesis of CNV and thereby account for leakage in the retina, in some embodiments featuring a combined therapy, the treatment strategy for CNV secondary to noninfectious inflammations would be directed at controlling the inflammatory process. Accordingly, systemic medications, for example, corticosteroids such as dexamethasone (e.g., Ozurdex) and derivatives thereof, with or without immunosuppressive agents may be indicated along with APC. Additionally, or alternatively, therapies aimed directly at the neovascular process, such as any of the intravitreal anti-VEGF agents, are indicated, particularly when the anti-inflammatory therapy shows an insufficient response. For example, in embodiments where CNV is associated with recurrent retinochoroiditis, the classical association of anti-toxoplasmic antibiotics with corticosteroids may be given to a patient, optionally, together with anti-VEGF therapy. Combined therapy comprising anti-inflammatory and anti-VEGF therapy aimed directly at the neovascular process is recommended in severe cases. Non-limiting examples of anti-VEGF agents that can be used in a combined treatment modality include bevacizumab, ranibizumab and aflibercept.

Without being limited by any theory, it is believed that APC interacts with cellular receptors such as protease activated receptor (PAR)1, PAR3, endothelial protein C receptor (EPCR) and others, and induces signal transduction that leads to barrier protection and stabilization. Anti VEGF agents, on the other hand, bind to VEGF and inhibit its ability to bind and activate VEGF receptors. In view of these different modes of action, combined treatment featuring co-administration of one or more anti-VEGEF agents and APC may have synergistic effects in treating or preventing CNV. In some embodiments, use of APC as the sole active agent in treatment of ocular diseases, disorders and condition associated with CNV is applied to anti-VEGF resistant patients.

In some exemplary embodiments, when CNV is secondary to an autoinflammatory disorder, APC can be administered to a patient tougher with immunosuppressive agents for example an association of steroids, cyclosporine A and, in some cases, azathioprine. The steroids may be periocular or systemic steroids.

In some exemplary embodiments, in idiopathic choroidal neovascularization (ICNV), where CNV is the only reliable finding in the retina and no other abnormalities are detectable, APC treatment can be combined with anti-inflammatory medications.

Since the inflammatory process is not only loco-regional and the whole immune system appears to be involved, the use of systemic steroids should be always considered. The safety and efficacy of immunosuppression for the control of choroidal new vessels are known. The choice of the immunosuppressant should be established on the basis of the characteristics of the drug itself. For example, mycophenolate mofetil (MMF) can be the choice of drug for the long-term control of inflammatory CNV since it has proven to be effective in improving arteriolopathy and decreasing the amount of soluble mediators involved in CNV pathophysiology.

Platelet derived growth factor (PDGF) plays an important role in the angiogenesis cascade that is activated in retinochoroidal vascular diseases (Ali Sadiq et al., 2015, http://dx.doi.org/10.1016/j.sjopt.2015.05.005). One possible explanation for the involvement of PDGF in the CNV process includes entry of platelets and monocytes into the vitreous and subretinal space upon injury to the blood-retina barrier, with subsequent platelet aggregation and PDGF discharge. Interleukins such as IL-1 and TGF-B, released from activated macrophages may lead to further synthesis of PDGF.

In some embodiments of combined therapy in accordance with the present invention, APC may be co-administered with anti-PDGF agents that block the effects of PDGF in the angiogenesis process in the retina. Non-limiting examples of anti-PDGF agents include PDGF antagonists, such as designed ankyrin repeat protein (DARPin) that selectively binds to and antagonizes PDGF-BB in subretinal CNV, optionally co-administered with a similar protein that antagonized VEGF-A (anti-VEGF protein). A further exemplary high affinity PDGF antagonist is E10030, which binds to PDGF and blocks its binding to PDGFR-β. This antagonist has increased effectiveness when co-administered with an anti-VEGF agent such as ranibizumab.

In some embodiments of the combined therapy, APC is provided to a patient together with one or more treatments selected from anti-angiogenesis, anti-inflammatory, anti-bacterial, immunosuppressive, anti PDGF, anti-fungal and viral therapies. In some embodiments, the co-administered active agent or drug is administered together with APC in a single dosage form, optionally by intravitreal injection. Additionally or alternatively, the co-administered active agent or drug is administered in one or more separate dosage forms, either before, simultaneously with or after administration of APC. In some embodiments, the co-administered active agent is administered systemically. Alternatively or additionally the co-administered active agent is administered locally, optionally by intravitreal injection.

Embodiments of the method of treatment described herein feature a regimen of APC administration dictated by various considerations such as the state of the retina, the progress of healing, tolerance of the patient and the like. For example, a single dose may be applied once a month or once a week for up to 6 to 8 weeks, wherein the gap between successive administrations and necessity of continuing APC administration is determined based on the state of the treated retina, progression of healing and side effects evaluated.

Pharmaceutical Compositions

In an aspect of some embodiments, there is provided a pharmaceutical composition comprising, as the active agent, APC, a functional fragment of APC, an APC derivative, an APC homolog or a combination thereof, for use in treatment of ocular diseases and disorders.

In some of any of the embodiments of the present invention, the pharmaceutical composition described herein is used in treatment of ocular diseases and disorder that are associated with, or caused by CNV, such as, but not limited to, age-related macular degeneration (AMD), angioid streaks and high myopia.

The pharmaceutical compositions described herein may comprise, besides the active agent APC, a pharmaceutically acceptable carrier and excipients and optionally further comprise chemical components which, for example, facilitate sustained release of the active agent in the treated eye.

Accordingly, in any of the methods and uses described herein, wild type APC or any of its functional partial sequences (fragments), derivatives and homologs described herein can be provided to an individual either per se, or as part of a pharmaceutical composition where it is mixed with a pharmaceutically acceptable carrier.

As used herein a "pharmaceutical composition" refers to a preparation of one or more of APC, a functional fragment, a derivative or a homologs thereof described herein (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject. The term "active ingredient" refers to a compound, which is accountable for a biological effect.

As used herein, the term "physiologically acceptable" means approved by a regulatory agency of the Federal or a state government or listed in the U.S. Pharmacopeia or other generally recognized pharmacopeia for use in animals, and more particularly in humans. Herein, the phrase "physiologically suitable carrier" refers to an approved carrier or a diluent that does not cause significant irritation to an organism and does not abrogate the biological activity and properties of a possible active agent.

Herein the term "excipient" refers to an inert substance added to a pharmaceutical composition to further facilitate processes and administration of the active ingredients. Examples, without limitation, of excipients include calcium carbonate, calcium phosphate, various sugars and types of starch, cellulose derivatives, gelatin, vegetable oils and polyethylene glycols Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1)

The pharmaceutical composition may be formulated for administration in either one or more local routes depending on the area to be treated.

In some embodiment, the pharmaceutical composition is formulated in a form suitable for intravitreal administration. In some embodiments, the pharmaceutical composition is formulated in a form suitable for topical application on the applied area.

According to an embodiment, the pharmaceutical composition described hereinabove is packaged in a packaging material and identified in print, in or on the packaging material, for use in the treatment of a medical condition associated with CNV.

Activate Protein C (APC)

Protein C may be purified from clotting factor concentrates or from plasma by well-known methods, and then activated in vitro to obtain the activated form APC, however such processes are complex and expensive, in part due to the limited availability of the starting material and the low concentration of protein C in plasma. Furthermore, the therapeutic use of products derived from human blood carries the risk of disease transmission. Thus, in some of any of the embodiments of APC use in therapeutic applications in accordance with the present invention, the APC used is a commercially available human recombinant wile-type APC, functional partial sequences thereof, derivatives thereof and variants (mutants) thereof obtained by known genetic engineering techniques, such as recombinant DNA techniques.

In some embodiments of the present invention, the full-length, wild-type human recombinant APC is applied for treatment of ocular diseases, disorders or conditions associated with CNV. Alternatively or additionally, a polymorphic variant or an interspecies homolog of human APC is applied.

In some embodiments, a functional fragment of wild-type human APC is applied in therapy of ocular diseases, disorders or conditions associated with CNV. As defined herein "a functional fragment of APC", is a partial sequence of the wild type protein sequence or of a polymorphic variant or of an interspecies homolog thereof. The functional fragment can comprise to 95%, up to 90%, up to 85%, up to 80%, up to 75% or even lesser of the wild-type APC amino acid sequence, and it maintains wild type or near wild type APC functionality.

In some embodiments, a derivative of the wild-type APC or of a functional partial sequence thereof is applied for therapeutic purposes in accordance with the present invention. As used herein, "a derivative of APC" encompasses wild-type APC, a polymorphic variant and an interspecies homolog thereof, or any functional partial sequence thereof, in which the amino acid sequence has been modified post protein synthesis, having substantially the same biological activity as wild-type APC. The phrase "having substantially the same biological activity" as used herein refers to APC derivatives having about 60% identical, about 65% identical, about 70% identical, about 75% identical, about 80% identical, about 85% identical, about 90% identical, about 95% identical, or 100% identical biological activity as wild type human activated protein C.

Post synthesis modification of APC or functional partial sequence thereof comprises chemical or physical modifications, or both, of one or more amino acids. APC or a functional partial sequence thereof that have undergone a chemical or physical modification are also termed herein "a chemical derivative" and "a physical derivative", respectively. For example, a derivative of the APC amino acid sequence may be identical to the wild type sequence, but contains a post-synthesis conformation modification (i.e., a physical derivatization).

Examples of APC derivatives useful for the purpose of the present invention are further discussed and disclosed, for example, in U.S. Pat. No. 5,516,650.

In some embodiments, a variant of the wild-type APC or of a functional partial sequence thereof is applied for therapeutic purposes in accordance with the present invention. As used herein, the terms "a variant of APC" and "an APC mutant" are interchangeable and encompasses wild-type APC, a polymorphic variant and an interspecies homolog thereof, or any functional partial sequence thereof, in which one or more of the naturally coded amino acids has been substituted or deleted via post translation modification. "A variant of APC" or "an APC mutant" further includes the naturally coded amino acids sequence containing additional one or more amino acids.

Post translation substitution modification comprises replacement of one or more naturally coded amino acids of APC with one or more amino acids selected from natural and non-natural amino acids. Post translation addition modification comprises addition of one or more amino acids selected from natural and non-natural amino acids to the naturally coded amino acid sequence. Modification resulting in substitution, addition or deletion of one or more amino is also referred to herein as "biological derivatization".

The term "natural amino acid" as used herein and in the art refers to the 20 naturally encoded and common aminoacids (alanine, arginine, asparagine, aspartic acid, cysteine, glutamine, glutamicacid, glycine, histidine, isoleucine, leucine, lysine, methionine, phenylalanine, proline, serine, threonine, tryptophan, tyrosine, and valine) as well as to pyrolysine and selenocysteine. "Non-natural amino acids" as used herein include, but are not limited to, amino acid analogs that function in a manner substantially similar to the naturally occurring aminoacids. Aminoacid analogs refer to compounds that have the same basic chemical structure as a naturally occurring amino acid, by way of example only, an α-carbon that is bound to a hydrogen, a carboxyl group, an amino group, and an R group. Such analogs may have modified R groups (by way of example, norleucine) or may have modified peptide backbones, while still retaining the same basic chemical structure as a naturally occurring aminoacid. Non-limiting examples of amino acid analogs include homoserine, norleucine, methionine sulfoxide, methionine methyl sulfonium.

The term "non-natural amino acid" further includes naturally encoded amino acids (including but not limited to, the 20 common amino acids, pyrrolysine and selenocysteine) as well as amino acid analogs that have undergone chemical modifications. Non-limiting examples of chemically modified amino acids include N-acetylglucosaminyl-L-serine, N-acetylglucosaminyl-L-threonine, and O-phosphotyrosine.

Post-translation modification of the APC protein may include an "amino terminus modification group", namely attachment of a molecule to the protein's terminal amine group. By way of example only, terminus modification groups include polyethylene glycol or serum albumin. Terminus modification groups may be used to modify therapeutic characteristics of APC, including but not limited to increasing the serum half-life of APC.

Individual substitutions, deletions or additions to the protein sequence which alters, adds or deletes a single natural amino acid or a small percentage of natural amino acids in the encoded APC sequence is considered herein a "conservatively modified variant" of APC where the alteration results in the deletion of an amino acid, addition of an amino acid, or substitution of a natural with a chemically similar (analog) amino acid.

In some embodiments, the APC derivative comprises a substitution, addition or deletion or any combination thereof, of amino acids, which provide one or more of the following features to the protein: increased affinity for a receptor, increased stability, modified (e.g., increased) aqueous solubility, increased solubility in a host cell, modulated protease resistance, modulated serum half-life, modulated immunogenicity, and/or modulated expression relative to the wild-type APC. Modulated biological activity as used herein refers to increasing or decreasing the reactivity, altering the selectivity, and enhancing or decreasing the substrate selectivity of APC and any functional parts thereof.

Usually, the modifications affected have beneficial effects on APC, such as improving its stability and/or its biological activity. Furthermore, APC is known to be associated with apoptosis in certain cellular systems. Alleviating or preventing cell damage associated at least in part with apoptosis, especially in subjects at risk for or suffering from such cell damage, may be affected by the use of APC mutants, for example, but not limited to, variants of recombinant APC that have markedly reduced anticoagulant activity, but retain near normal anti-apoptotic (cytoprotective) activity, so that the ratio of anti-apoptotic to anticoagulant activity is greater in the variants than it is in wild-type or endogenous activated protein C. Three examples of such recombinant APC mutants disclosed in U.S. Pat. Nos. 9,192,657 and 7,489,305 are KKK191-193AAA-APC (mutation of lysines 191, 192 and 193 to alanines in a surface-exposed loop containing Lys191-193; also known in that are as "3K3A-APC"), RR229/230AA-APC (mutation of arginines 229 and 230 to alanines), and RR229/230AA plus KKK191-193AAA-APC (combination of mutations of arginines 229 and 230 to alanines and lysines 191, 192 and 193 to alanines (also known in the art as "5A-APC")). Given their reduced anticoagulant activity, these exemplary APC variants provide significantly reduced risk of bleeding (variants 5A-APC and 3K3A-APC have <10% residual anticoagulant activity). 3K3A-APC has been reported to provide neuroprotection and extended the therapeutic window, (Griffin et al., 2015, Blood, 125:2898-2907). Other APC mutants that may be used in accordance with some embodiments include APC-2Cys, and K193E-APC, E149A-APC disclosed in Griffin et al. (supra), and APC variants that include the substitution of residue 158 (Asp) with a non-acidic amino acid residue such as Ala, Ser, Thr or Gly, or a substitution of residue 154 (His) with an amino acid residue such as Lys, Arg or Leu.

A modified wild-type APC can feature a chemical derivatization, physical derivatization, a biological derivatization or any combination thereof. In some embodiments, such derivatizations are regioselective. In some embodiments, such derivatizations are regiospecific.

The sequence of the APC chemical, physical or biological derivative can be at least 70%, at least 80%, at least 85%, at least 90%, at least 95%, at least 98%, or even 100% identical to the wild type APC sequence or any of the functional partial sequences thereof.

In some embodiments, the biological activity of any of the APC derivatives is improved by about 5%, about 10%, about 15%, about 20%, about 30%, about 50%, about 60%, about 70%, about 80%, about 85%, about 90%, about 95%, about 100%, about 110%, or more, including any intermediate values therebetween, compared to the biological activity of any of the wild type ACP or functional partial sequence thereof.

The form "modified or unmodified" means that the natural amino acid sequence being discussed is optionally modified, that is, the natural amino acid sequence of APC under discussion can be modified or unmodified Embodiments described herein contemplate to the use of commercially available APC derivatives.

It is expected that during the life of a patent maturing from this application many relevant chemical, physical and biological derivatives of APC or of functional partial sequences thereof will be developed and the scope of the term "activated protein C, functional partial sequence thereof, derivative thereof or variant thereof" is intended to include all such new technologies a priori.

The terms "comprises", "comprising", "includes", "including", "having" and their conjugates mean "including but not limited to".

The term "consisting of" means "including and limited to"

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Various embodiments and aspects as delineated hereinabove and as claimed in the claims section below find experimental support in the following examples.

EXAMPLES

Reference is now made to the following examples, which together with the above descriptions illustrate some embodiments in a non-limiting fashion.

Materials and Methods

Cell Culture.

Human retinal pigment epithelial (RPE) cells (ARPE-19 cell line) were purchased from ATCC (Manassas, Va.) and cultured under standard conditions according to the manufacturer's instructions. Growth media: DMEM/F-12 (HAM) 1:1 (Biological Industries, Israel cat #01-170-1A) supplemented with 10% Fetal bovine serum (Biological Industries, Israel cat #04-121-1A), Glutamine 1 mM (Biological Industries, Israel cat #03-022-1B), 100 u/ml penicillin, 0.1 mg/ml streptomycin and 12.5 u/ml nystatin (Biological Industries, Israel cat #03-032-1B). Experiments were performed using passages 10-30. For immunofluorescence assay, cells were plated at a concentration of $1.3 \times 10^4$ cells/cm$^2$ and grown for a minimum of 30 days, wherein the media was exchanged every 2-3 days. Cells were washed with starvation medium (cells complete growth medium lacking serum), and treated with 0.1, 1.0, or 10 µg/ml activated protein C (APC) in starvation medium for 10 minutes. After 10 minutes, the medium was replaced with complete growth medium and the cells were incubated for up to 4 hrs.

Human Activated Protein C (APC).

Human recombinant wild-type APC was purchased from Haematologic Technologies Inc. USA (cat #HCAPC-0080).

In Vitro Permeability Assay.

RPE cells were plated at a concentration of $6.7 \times 10^3$ cells/cm$^2$ on a 1 µm polyethylene terephthalate (PET) Transwell® insert (millicell, Millipore Corporation, Switzerland). The cells were grown for 30 days to confluency in 600 µl medium in the lower chamber and 100 µl in the upper chamber. Medium was exchanged every 2-3 days. Cells were then washed with starvation medium (basal medium containing 1 mM glutamine, 100 u/ml penicillin, 0.1 mg/ml streptomycin and 12.5 un/ml nystatin), and incubated with starvation medium containing 10.0, 1.0, 0.1 or 0.0 µg/ml APC. Following 10 minutes incubation with APC, the upper chamber medium was replaced with fluorescein isothiocyanate (FITC) Dextran 70 kD, 1000 µg/ml (Sigma, Israel, cat #FD-70) for up to 6 hours. The lower chamber medium was replaced with basal medium. Medium samples from the lower part of the insert were taken. FITC fluorescence, representing flow across the cell layer, was detected using a multi-detection microplate reader (Synergy™ HT, BioTek) at 485 nm excitation. Medium samples were returned to the lower chamber for further incubation.

For calculation of FITC-Dextran concentration, the fluorescence was compared to a calibration curve.

In Vitro Zonula Occludens-1 (ZO-1) Immunostaining.

Cells were cultured on the 4 wells microscope slide Permanox™ Plastic Chamber Slide System (Thermo Scientific, USA cat #177437) for 30 days. The cells were washed with starvation medium, incubated with starvation medium containing 1.0, 0.1, or 0.0 µg/ml APC for up to 4 hrs, then fixed in 4% paraformaldehyde in phosphate buffer saline (PBS) and, finally, permeabilized with 0.2% of the nonionic surfactant Triton™ X-100 in PBS for 10 minutes. Prior to antigen application, antigen retrieval was performed using 10 mM citric acid pH 6.0 for 10 minutes at 95° C. The demonstration of the antigen was significantly improved by pretreatment with the antigen retrieval reagents that broke the protein cross-links formed by paraformaldehyde fixation and thereby uncovered hidden antigenic sites. The samples were incubated with rabbit anti ZO-1 antibody (Invitrogen, cat #40-2300, 1:100), overnight at 4° C. in humidified chamber, followed by incubation with the secondary antibody Alexa Fluor® 568 donkey anti rabbit antibody (Invitrogen, Cat #A10042, 1:100) for 1 hour at room temperature, and 5 min incubation with NucBlue® Fixed Cell ReadyProbe® reagent (Molecular Probes™, USA; cat #R37606) diluted in PBS. Images of representative slides were captured digitally using standard microscope and camera settings. For 3 dimensional (3D) confocal images, 0.5 µm distance Z stack images of cells were captured (Leica TCS SP8). Three-dimensional representation of images was achieved using the scientific software module Imaris x 64 7.1.1 (Oxford Instruments, UK).

In Vivo Laser Animal Models.

Choroidal laser photocoagulation is an accepted and commonly used method for the induction of choroidal neo vascularization (CNV). Eight weeks old pigmented male C57BL/6J mice were obtained (Harlan Laboratories Ltd., Jerusalem, Israel) and handled according to recommendations of the hospital's Institutional Animal Care and Use Committee. Animals were anesthetized with intraperitoneal (IP) injection of 100 mg/kg ketamine and 10 mg/kg xylazine, and the pupils were dilated with topical administration of 0.8% tropicamide eye drops. Laser applications were applied using an indirect diode laser ophthalmoscope (IRIS Medical™ Oculight® SLx System, Iridex, Mountain View, Calif., USA) with the treatment beam set at 810 nm. Light rays were focused onto the retinal surface by condensing lenses of 90 diopters (D) (Volk® Optical, Mentor, Ohio, USA). CNV was induced using laser power of 350 mW for 100 msec on the right eyes at the 3, 6, and 9 o'clock positions of the posterior pole, at a distance of 1-2 optic disc diameters (DD) surrounding the optic nerve. Formation of white bubble was confirmed by the operator. Following laser application, APC was intravitreally injected under an operating microscope. A microsyringe (33-gauge; Hamilton®) was placed intravitreally in the retro lateral space of the eye and at least one of the following was injected: 1 μl (per mice) of APC (1 μg/μl); saline (as control); and bevacizumab (Avastin®) (25 μg/l μl) (Genentech, Inc., South San Francisco, Calif., USA and Roche, Basel, Switzerland); Flat mounts were performed on days 5 post laser applications.

Dextran Perfusion and Flattening of Choroid/Retina.

Five post laser applications, mice were anesthetized as described above. For dextran perfusion, 0.1 ml fluorescein isothiocyanate dextran conjugate (FITC-dextran; MW 500 k, Sigma Aldrich, Rehovot, Israel), diluted in saline to a concentration of 25 mg/ml, were injected to the left ventricle of hearts of anesthetized mice. Eyes were enucleated, washed in PBS and fixed in 4% formalin for 2-3 hrs. Neuronal retinas were peeled. Three to 4 radial incisions were used to flatten the RPE-choroid-sclera complex or the neuronal retina on glass slides. Slides were covered with the mounting medium ProLong®™ Gold antifade reagent (Invitrogen, USA), or further stained with antibodies, as described below.

Immunostaining of Flat Choroid/Retina.

For further staining of flattened choroid/retina with antibodies, slides obtained as described above were washed with PBS and incubated in a PBS-Triton™ X100 0.5% solution at 4° C. overnight. Slides were then blocked for 1 hour in 5% normal donkey serum (NDS) and incubated with rat anti-mouse CD31 (eBioscience®, San Diego, Calif., USA, cat #14-0311) 1:100 at 4° C. overnight. Slides were then washed with PBS and incubated at 4° C. overnight with goat anti rat Alexa Fluor® 568 1:100 (Invitrogen), further incubated for 15 minutes with 10 μg/ml the nucleic acid dye 4',6-Diamidino-2-phenylindole dihydrochloride (DAPI) in PBS (Sigma, cat #9542), and covered with mounting medium ProLong®™ Gold antifade reagent.

Images of flat choroid were captured using a fluorescence microscope. Flat choroids were also captured with light microscope, to eliminate areas transparent to light, presumably areas injured during flat mount preparations.

The CNV area was quantified with Image-J software (NIH, Bethesda, Md., USA). Area of lesions was delineated. Analysis of variance was used for statistical analysis using one-way ANOVA test.

Images of 3D projections were captured using Leica TCS SP8 confocal microscope. One micrometer (1 μm) distance Z stack images of flattened retinas/choroid were taken under standard conditions. Volume and depth of staining was measured using Imaris software.

Example 1

The Effects of APC on Cellular Localization of the Tight Junction Protein Zonula Occludens 1 (ZO-1)

Intercellular junctional complexes include tight junction proteins, such as occludin or claudins. These proteins bind to the cytoplasmic phosphoprotein zona occludens (ZO)-1, which links to the cytoskeleton and thereby provides junctional stability. Disruption of ZO-1 may lead to breakdown of tight junctions and an increase in vascular (endothelial) or epithelial permeability. In view of the involvement of ZO-1 in linking the tight junction complex to the cytoskeleton and in maintaining RPE's barrier integrity, the effect of exposure to APC on the cellular localization of ZO-1 was analyzed. Cellular localization of ZO-1 was studied using immunofluorescence staining with anti-ZO1 antibody as described in Materials and Methods" above.

Confocal microscope images of RPE cells stained with rabbit anti ZO-1 antibody (bright lines) and with NucBlue® Fixed Cell ReadyProbe® reagent, (nuclear staining) with or without APC (0-10 μg/ml) are shown in FIGS. 2A-2D. It is clearly seen that 1 μg/ml APC induced up regulation, translocation and accumulation of ZO-1 protein in the ARPE19 cell membrane. These results suggest that ZO-1 accumulation in the peripheral membrane of epithelial cells may inhibit pathological permeability and angiogenesis through physical barrier formed by tight junction structure.

Example 2

Effects of APC on Permeability of RPE Cells In Vitro

To address the question whether the translocation of ZO-1 is accompanied by decrease in RPE permeability, cell permeability was evaluated based on spectrophotometric monitoring of the transport of labeled dextran across a cell layer in the absence or presence of APC. In vitro permeability of ARPE-19 cells was assayed according to the protocol described above in Material and Methods.

Figure 3:
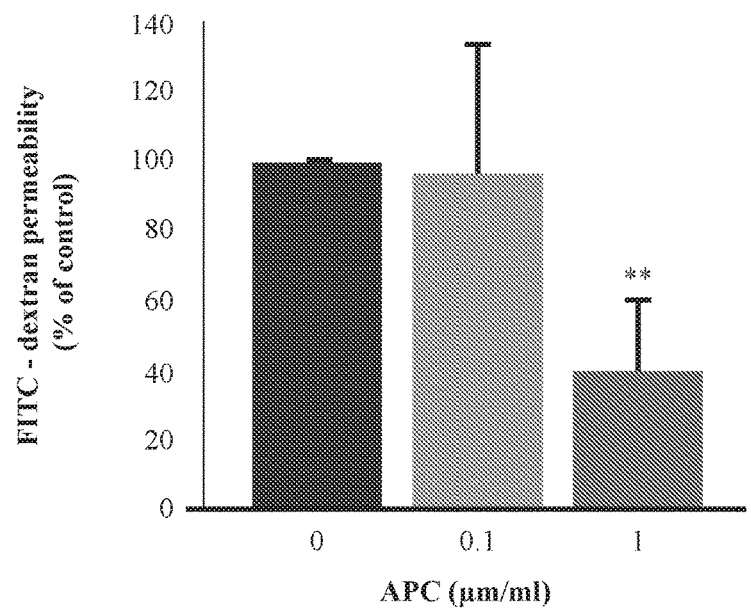
FIG. 3 is a graph showing the FITC-dextran permeability (as % of control) of ARPE-19 cells treated with 0.0, 0.1 or 1 µg/ml APC (average results of 4 experiments).

The results of 4 repeated experiments are summarized in FIG. 3. As shown, exposure of RPE cells to 1 μg/ml APC dramatically reduced leak of FITC-Dextran through the RPE monolayer, clearly implying that APC stabilized the RPE barrier.

Example 3

Quantitation of CNV Area Following Laser Photocoagulation

Choroidal neo vascularization (CNV) was induced by indirect diode laser photocoagulation on male C57BL/6J mice as described above in Materials and Methods. Immediately following injury, mice were injected intravitreally with 1 μl APC at 1 μg/animal or 1 μl bevacizumab at 25 μg/animal. CNV area of flat choroid was determined using anti CD31 antibody immunofluorescence staining as described in Materials and Methods. Cluster of differentiation 31 (CD31, also known as platelet endothelial cell adhesion molecule (PECAM-1)), is a protein that makes up a large portion of endothelial cell intercellular junctions. In immunohistochemistry, CD31 is used primarily to demonstrate the presence of endothelial cells that are the "building-blocks" of the CNV. CNV area was evaluated by imageJ photo processing software on day 5 post laser injury.

Figure 4:
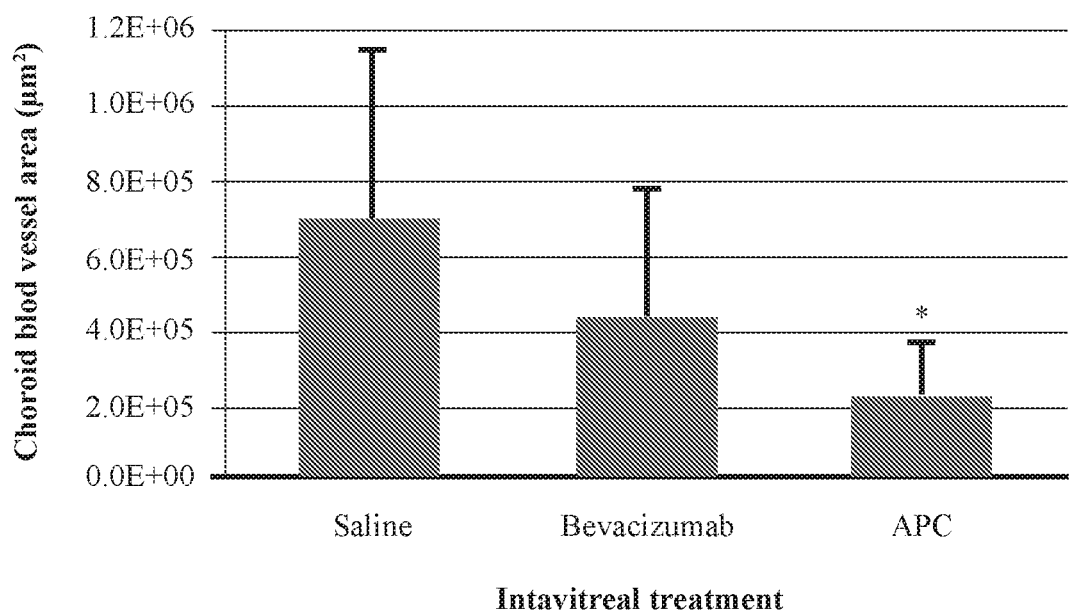
FIG. 4 is a graph showing choroid blood vessel area of flat choroid following laser photocoagulation of the retina and intravitreal injections of saline, bevacizumab (25 µg/animal) or APC (1 µg/animal).

As shown in FIG. 4, APC treatment dramatically reduced CNV area. The APC effect was comparable to the effect of bevacizumab, the current treatment of choice for CNV.

Example 4

Effect of APC Treatment on CNV Volume and Depth (3-Dimension Analysis)

CNV was induced by indirect diode laser photocoagulation on male C57BL/6J mice as described above in Materials and Methods. Immediately following injury, mice were injected intravitreally with either 1 μl APC at 1 μg/animal or 1 μl saline. Five days after laser applications mice were anesthetized, and 0.15 ml Fluorescein isothiocyanate dextran conjugate (FITC-Dextran), diluted in saline to a concentration of 25 mg/ml, were injected into the left ventricle of each rat's heart. Eyes were enucleated. The choroid-RPE and the retina were separated, flattened on slides and mounted as described in Materials and Methods. Images were acquired using a confocal microscope. Quantification of CNV was performed on 3D-reconstructed images using 3D image analysis software.

Figure 5A:
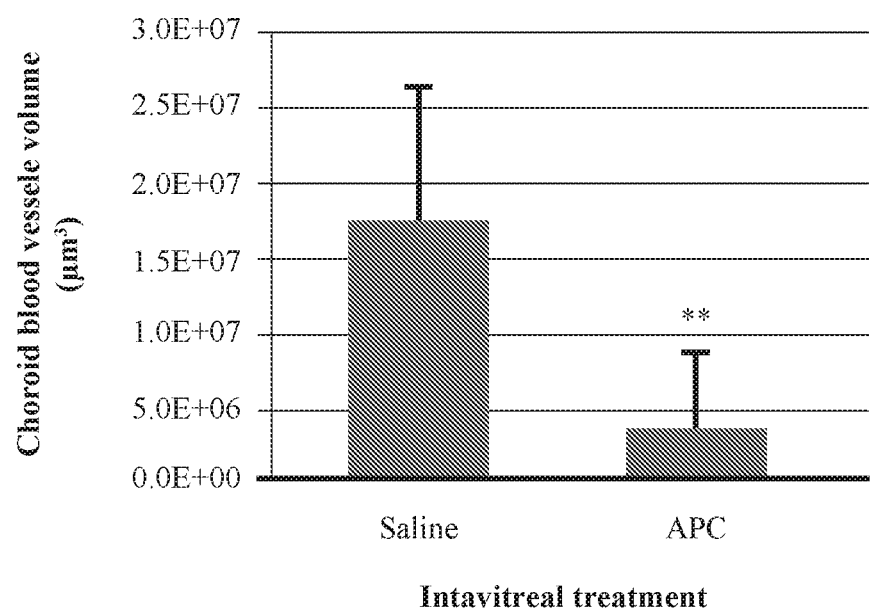
FIGS. 5A-5B are graphs showing blood vessel volume (5A) and depth (5B) of flattened choroid-RPE sections following laser photocoagulation and intravitreal injections of saline, or APC (1 µg/animal)
Figure 5B:
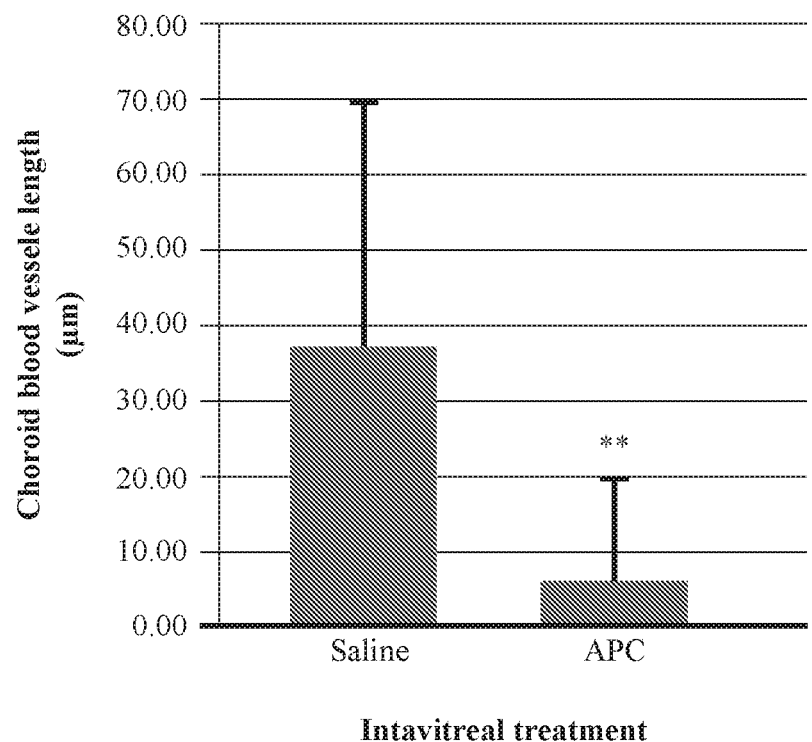

FIGS. 5A and 5B shows the quantification of CNV volume (5A) and depth (5B) in the choroid-RPE sections. It is clearly demonstrated that APC treatment dramatically reduced CNV volume and depth.

Example 5

Effect of APC on Penetration of Newly Formed Blood Vassals from Choroid into the Retina (3D Analysis)

Choroidal neo vascularization was induced in male C57BL/6J mice. Immediately following injury, mice were injected intravitreally with either 1 μl APC at 1 μg/animal or 1 μl saline, and dextran perfusion and flattening of retina were conducted as described above in Materials and Methods. One micrometer (1 μm) distance Z stack images of flattened retinas were taken under standard conditions. A summary of Z section measurements of the entire retina 5 days after photocoagulation and following perfusion with dextran is presented in FIG. 6A-6C.

Figure 6A:
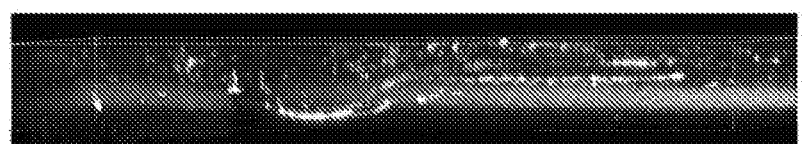
Figure 6B:
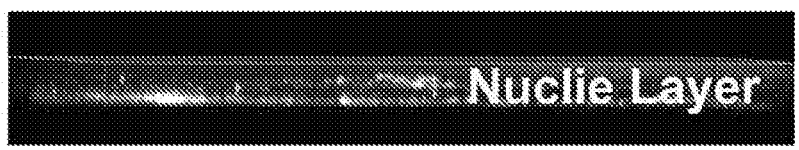

Representative images of entire retina shown in FIGS. 6A-6B demonstrate the appetence of blood vessels at the deeper section of the retina induced by the laser and its inhibition by APC.

Quantification of blood vessels area measurements in the retinal section is shown in FIG. 6C. As clearly shown, APC reduced significantly the penetration of blood vassals to the retina.

Although the invention has been described in conjunction with specific embodiments thereof, it is evident that many alternatives, modifications and variations will be apparent to those skilled in the art. Accordingly, all alternatives, modifications and variations that fall within the spirit and broad scope of the appended claims are encompassed herein.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for therapy of at least one of retinal leakage or choroidal neovascularization (CNV) in a subject, the method comprising administering to the eye of the subject a therapeutically effective amount of activated protein C (APC), thereby providing therapy to the subject.

2. The method according to claim 1, wherein the therapy is treatment of retinal leakage and CNV associated with an ocular disease, disorder or condition.

3. The method according to claim 2, wherein the ocular disease, disorder or condition is characterized by being at least one of: caused directly by CVN; featuring CNV as a secondary stage or a complication thereof; or featuring CNV as a synchronous or asynchronous sequela thereof.

4. The method according to claim 3, wherein the ocular disease, disorder or condition is
- an ocular disease that is at least one of age-related macular degeneration (AMD) associated with choroidal neovascularization, pathologic myopia, pseudoxanthoma elasticum with angioid streaks, noninfectious uveitis, infectious uveitis, an inflammatory disease of the optic nerve selected from the group consisting of optic neuritis, papilledema, anterior and ischemic optic neuropath (AION), Behçet's disease or retinopathy;
- an ocular disorder that is caused by at least one of chronic inflammation, oxidative damage, drusen biogenesis, lipofuscin accumulation, abnormalities of Bruch's membrane, vascular changes in the eye that impede regulation of blood pressure and flow and create conditions of ischemia, physiologic aging, genetic factors or environmental factors; or
- an ocular condition that is an accidental, occasional incidence in which choroidal neovascularization and retinal leakage develop following a traumatic injury of the retina, or complications during an ophthalmic medical procedure.

5. The method according to claim 4, wherein the ocular disease is AMD associated with choroidal neovascularization.

6. The method according to claim 1, wherein the therapy is a combined therapy further comprising administration of one or more active agents selected from the group consisting of an anti-angiogenesis, anti-inflammatory, anti-bacterial, immunosuppressive, anti-PDGF, anti-fungal and anti-viral agent.

7. The method according to claim 6, wherein the anti-angiogenesis agent is anti-VEGF agent or platelet derived growth factor (PDGF) inhibitor, and the immunosuppressive agent is a steroid.

* * * * *